United States Patent
DeLoach et al.

(10) Patent No.: US 12,264,230 B2
(45) Date of Patent: Apr. 1, 2025

(54) CYCLOHEXANE DICARBOXYLATE MIXED ESTER COMPOSITIONS USEFUL AS PLASTICIZERS

(71) Applicant: Eastman Chemical Company, Kingsport, TN (US)

(72) Inventors: Joseph Alexander DeLoach, Jonesborough, TN (US); Curtis Louis Schilling, III, Kingsport, TN (US); Thomas John Markley, Kingsport, TN (US)

(73) Assignee: Eastman Chemical Company, Kingsport, TN (US)

( * ) Notice: Subject to any disclaimer, the term of this patent is extended or adjusted under 35 U.S.C. 154(b) by 466 days.

(21) Appl. No.: 17/595,327

(22) PCT Filed: Jun. 12, 2020

(86) PCT No.: PCT/US2020/037375
§ 371 (c)(1),
(2) Date: Nov. 15, 2021

(87) PCT Pub. No.: WO2020/263595
PCT Pub. Date: Dec. 30, 2020

(65) Prior Publication Data
US 2022/0185989 A1    Jun. 16, 2022

Related U.S. Application Data

(60) Provisional application No. 62/866,740, filed on Jun. 26, 2019.

(51) Int. Cl.
C08K 5/12 (2006.01)
C07C 69/75 (2006.01)
C08K 5/00 (2006.01)

(52) U.S. Cl.
CPC ............... C08K 5/12 (2013.01); C07C 69/75 (2013.01); C08K 5/0016 (2013.01); *C07C 2601/14* (2017.05)

(58) Field of Classification Search
CPC ............................. C07C 69/75; C07C 2601/14
See application file for complete search history.

(56) References Cited

U.S. PATENT DOCUMENTS

| 4,489,188 | A | 12/1984 | Jones et al. | |
|---|---|---|---|---|
| 4,620,026 | A | 10/1986 | Siegel | |
| 4,950,702 | A | 8/1990 | Arendt | |
| 6,969,735 | B1 | 11/2005 | Godwin | |
| 7,208,545 | B1* | 4/2007 | Brunner | C07C 67/303 560/127 |
| 7,973,194 | B1* | 7/2011 | Kinkade | C08K 5/0016 560/127 |
| 9,403,965 | B2 | 8/2016 | Laufer et al. | |
| 2008/0058450 | A1 | 3/2008 | Stimpson et al. | |
| 2012/0181056 | A1 | 7/2012 | Chaudhary et al. | |
| 2013/0062094 | A1 | 3/2013 | Naert et al. | |
| 2015/0112008 | A1 | 4/2015 | Patiul et al. | |
| 2016/0096350 | A1 | 4/2016 | Lu | |
| 2016/0159051 | A1 | 6/2016 | Lu et al. | |
| 2016/0159057 | A1 | 6/2016 | Butler | |
| 2016/0160005 | A1 | 6/2016 | Lu et al. | |
| 2016/0160030 | A1 | 6/2016 | Chen et al. | |
| 2018/0105673 | A1 | 4/2018 | Schilling, III et al. | |
| 2019/0359789 | A1 | 11/2019 | Pfeiffer et al. | |
| 2022/0185989 | A1 | 6/2022 | Deloach et al. | |
| 2022/0325068 | A1* | 10/2022 | DeLoach | C08K 5/0016 |

FOREIGN PATENT DOCUMENTS

| EP | 3 333 219 A1 | 6/2018 |
|---|---|---|
| EP | 3 473 669 A1 | 4/2019 |
| EP | 3 476 890 A1 | 5/2019 |
| JP | H0350246 A | 3/1991 |
| JP | H05339413 A | 12/1993 |
| JP | 11302445 A * | 11/1999 |

(Continued)

OTHER PUBLICATIONS

Conn, R. C., et al.; "Some Aromatic Esters of the Monoalkyl Ethers of Ethylene Glycol and Diethylene Glycol"; Journal of the American Chemical Society, 54(11), 1932, pp. 4370-4372.
Ram, A. and Schneider, Z; "Flow Properties of PVC Plastisols"; Industrial & Engineering Chemistry Product Research and Development, 9(3); Sep. 1, 1970; pp. 286-291.
Sears, J. K. and Darby, J. R.; "The Technology of Plasticizers" 1982; pp. 104-107.
Co-pending U.S. Appl. No. 17/595,250, filed Nov. 12, 2021; Pinguan Zheng et al.
Co-pending U.S. Appl. No. 17/595,253, filed Nov. 12, 2021; Zhenpeng Li et al.
Co-pending U.S. Appl. No. 17/594,972, filed Nov. 4, 2021; Xhenpeng Li and Eric Jon Moskala.

(Continued)

*Primary Examiner* — Vickey Nerangis
(74) *Attorney, Agent, or Firm* — Tammye L. Taylor Polk; Pan Yuan

(57) ABSTRACT

The present application discloses novel cyclohexane dicarboxylate mixed esters of formula I: wherein $R^1$, $R^2$, and n are defined herein. The mixed esters are useful as plasticizers. The application also discloses resin compositions comprising the cyclohexane dicarboxylate mixed esters of formula I.

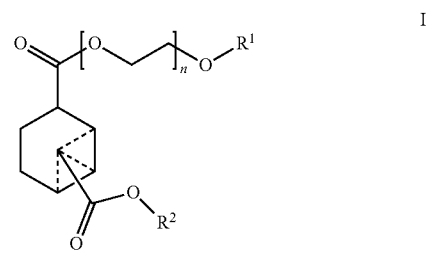

13 Claims, No Drawings

(56) References Cited

FOREIGN PATENT DOCUMENTS

| RU | 2015/156846 A | 7/2017 |
|---|---|---|
| RU | 2 633 963 C2 | 10/2017 |
| WO | WO 2007/021987 A1 | 2/2007 |
| WO | WO 2009/085453 A2 | 7/2009 |
| WO | WO 2016094203 A1 | 6/2016 |

OTHER PUBLICATIONS

Co-pending U.S. Appl. No. 17/594,969, filed Nov. 4, 2021; Joseph Alexander DeLoach et al.
Notification of Transmittal of the International Search Report and the Written Opinion of the International Searching Authority with Date of Mailing of Oct. 9, 2020 received in International Application No. PCT/US2020/037375.
Notification of Transmittal of the International Search Report and the Written Opinion of the International Searching Authority with Date of Mailing of Oct. 9, 2020 received in International Application No. PCT/US2020/037369.
Notification of Transmittal of the International Search Report and the Written Opinion of the International Searching Authority with Date of Mailing of Oct. 9, 2020 received in International Application No. PCT/US2020/037373.
Notification of Transmittal of the International Search Report and the Written Opinion of the International Searching Authority with Date of Mailing of Oct. 9, 2020 received in International Application No. PCT/US2020/037361.
Notification of Transmittal of the International Search Report and the Written Opinion of the International Searching Authority with Date of Mailing of Oct. 9, 2020 received in International Application No. PCT/US2020/037365.
Tan Jihuai et al: "Highly efficient and recyclable catalysts SnC12-Xh3pw12040/ac WITH Bronsted and Lewis acid sites for terephthalic acid esterification", Journal of the Taiwan Institute of Chemical Engineers, Elsevier, Amsterdam, NL; vol. 86, Mar. 31, 2018, pp. 18-24, Mar. 31, 2018.
Malik Sameena N et al: "Treatment of pharmaceutical industrial wastewater by nano-catalyzed ozonation in a semi-batch reactor for improved biodegradability", Science of the Total Environment vol. 678; Apr. 17, 2019; pp. 114-122.
Non-Final Office Communication received in U.S. Appl. No. 17/595,250 dated Jun. 10, 2024.

* cited by examiner

CYCLOHEXANE DICARBOXYLATE MIXED ESTER COMPOSITIONS USEFUL AS PLASTICIZERS

BACKGROUND OF THE INVENTION

The current general purpose non-phthalate plasticizer preference is bis(2-ethylhexyl) terephthalate ("DOTP"). It is a reasonable plasticizer but does not have acceptable performance in many legacy production processes. The current application discloses novel mixed cyclohexane dicarboxylate esters ("MCHDE") compositions which provide enhanced fusion capability relative to DOTP, while maintaining viscosity performance in polymer-plasticizer systems. The fusion performance is close to that of fast-fuser/general purpose plasticizer blends, and the MCHDE have an advantage in that they are less volatile than the aromatic counterparts.

SUMMARY OF THE INVENTION

The present application discloses a compound of formula I:

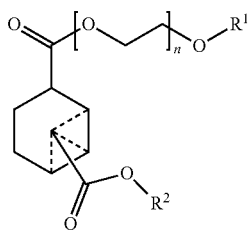

wherein:

$R^1$ is independently an unbranched or branched ($C_{1-9}$) alkyl; $R^2$ is independently an unbranched or branched (C1-8)alkyl; and n is independently 1, 2 or 3.

The present application discloses a plasticizer composition comprising: greater than 40 weight percent (wt %) of a compound of formula I:

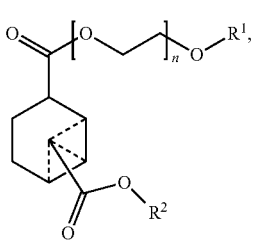

less than 30 wt % of a compound of formula II:

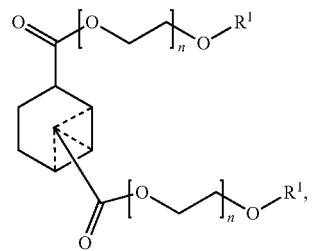

and less than 40 wt % of a compound of formula III:

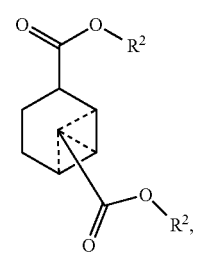

wherein:

each $R^1$ is independently an unbranched or branched ($C_{1-9}$)alkyl;

each $R^2$ is independently an unbranched or branched ($C_{1-12}$)alkyl;

and each n is independently 1, 2 or 3, wherein the wt % is determined based on the total weight of the plasticizer composition.

The application also discloses a resin composition comprising:

(I) a resin; and (II) a plasticizer composition comprising:

greater than 40 weight percent ("wt %") of a compound of formula I:

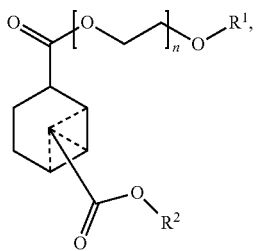

less than 30 wt % of a compound of formula II

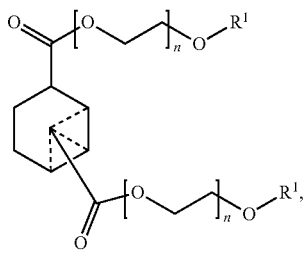

and
less than 40 wt % of a compound of formula III

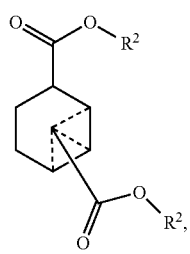

wherein:
each $R^1$ is independently unbranched or branched ($C_{1-9}$) alkyl;
each $R^2$ is independently unbranched or branched ($C_{1-12}$) alkyl; and
each n is independently 1, 2 or 3,
wherein the wt % is determined based on the total weight of the plasticizer composition.

DETAILED DESCRIPTION

Definitions

As used herein, the terms "a," "an," and "the" mean one or more. "Stabilizer" means any additive added to a formulation that helps to prevent color formation and degradation in the formulation. Classes of stabilizers include antioxidants, light stabilizers, acid scavengers, heat stabilizers, flame retardants, and biocides.

Antioxidants are chemicals used to interrupt degradation processes during the processing of materials. Antioxidants are classified into several classes, including primary antioxidant, and secondary antioxidant.

"Fillers" are materials added to formulations or compositions primarily to reduce cost, increase the output of dry blending, increase electrical resistance, increase resistance to ultra-violet light, increase hardness, provide improved heat transmission, and to increase the resistance of heat deformation. Fillers can also impact anti-blocking or anti-slip performance of the compositions. Nonlimiting examples of fillers included calcium carbonate, fly ash clays, silica, dolomite, bauxite, titanium dioxide. The particular particle size distribution and average surface area of the filler will be chosen according to the properties it is desired to impart, as would be apparent to one of skill in the art.

"Flame retardant" are materials that increase ignition time, reduce flame spreading and/or rate of burning. Examples of flame retardants that may be used include halogen containing compounds and phosphorous containing organic compounds such as triaryl, trialkyl or alkyl diaryl phosphate esters. Other materials that may be used include aluminum trihydrate, antimony oxides, molybdates, or zinc borate.

As used herein the term "chosen from" when used with "and" or "or" have the following meanings: A variable chosen from A, B and C means that the variable can be A alone, B alone, or C alone. A variable A, B, or C means for example that the variable can be A alone, B alone, C alone, A and B in combination, A and C in combination, B and C in combination, or A, B, and C in combination.

"Alkyl" groups suitable for use herein can be straight, branched, or cyclic, and can be saturated or unsaturated. Alkyl groups suitable for use herein include any ($C_{1-20}$), ($C_{1-12}$), ($C_{1-5}$), or ($C_{1-3}$) alkyl groups. In various embodiments, the alkyl can be a $C_{1-5}$ straight chain alkyl group. In still other embodiments, the alkyl can be a C1-3 straight chain alkyl group. Specific examples of suitable alkyl groups include, but are not limited to, methyl, ethyl, n-propyl, isopropyl, n-butyl, isobutyl, sec-butyl, tert-butyl, pentyl, hexyl, octyl, decyl, dodecyl, cyclopentyl, and cyclohexyl groups. "Alkylene" is a bivalent alkyl group.

As used throughout, when a group such as the R group is shown unattached with dotted lines as is show in diagram 1, the R group can be attached either to the one, two, three or four position of the ring system where the dotted line attaches as shown in (I). In one embodiment, the R group is attached either to the two, three, or four position of the ring system as shown in (II).

Diagram 1.

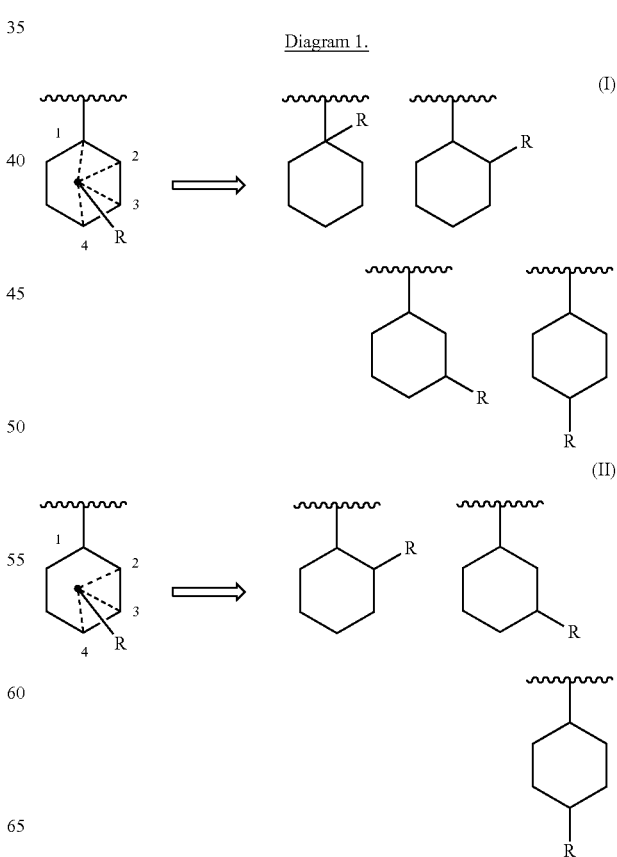

-continued

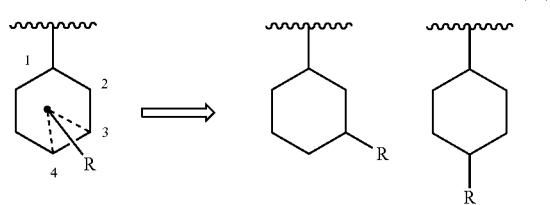
(III)

The term "plastisol", as used herein, refers to a liquid dispersion of polymeric resin particles, optionally with other ingredients, in a plasticizer. The term "fused plastisol", as used herein, refers to the solid plastic material that is formed upon fusing the plastisol and subsequently cooling to a desired temperature. The term "fusing", as used herein, refers to heating of the plastisol to a temperature sufficient to yield a solid structure with mechanical integrity.

In addition to the plasticizer, the plastisol comprises a resin. In one embodiment, the resin comprises poly(vinyl chloride) (polyvinyl chloride), poly(vinyl acetate), acrylic polymers and/or vinyl chloride-containing copolymers. In one embodiment, the polymeric component comprises poly (vinyl chloride) and/or poly(vinyl acetate). In another embodiment the polymeric component comprise poly(vinyl chloride) and vinyl chloride-containing copolymers comprising acrylic monomeric residues. In one embodiment, the polymeric component is poly(vinyl chloride).

One common use of polyvinyl chloride is in a plastisol. Plastisols are ubiquitous in the production of components for the flooring, medical, automotive, consumer products, and construction markets. Plastisols may utilize a wide range of plasticizer loadings, from 20 phr or less in semi-rigid applications, to 600 phr for very flexible formulations that produce fishing worms. Plastisols typically employ polyvinyl chloride resins with particle sizes in the range of 2 to 70 microns, which are commonly produced via emulsion polymerization.

Composition of Matter

The present application discloses a compound of formula I:

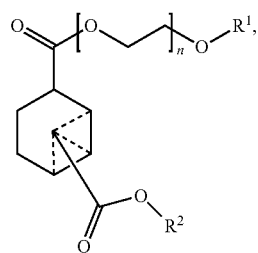
I

, wherein: each $R^1$ is independently an unbranched or branched $(C_{1-9})$ alkyl; $R^2$ is independently an unbranched or branched $(C_{3-8})$alkyl; and each n is independently 1, 2 or 3.

In one embodiment, $R^2$ is chosen from methyl, ethyl, unbranched or branched propyl, unbranched or branched butyl, unbranched or branched pentyl, unbranched or branched hexyl, unbranched or branched heptyl, or unbranched or branched octyl. In one class of this embodiment, $R^2$ is methyl. In one class of this embodiment, $R^2$ is ethyl. In one class of this embodiment, $R^2$ is propyl. In one class of this embodiment, $R^2$ is unbranched or branched butyl. In one class of this embodiment, $R^2$ is unbranched or branched hexyl. In one class of this embodiment, $R^2$ is unbranched or branched heptyl. In one class of this embodiment, $R^2$ is unbranched or branched octyl. In one subclass of this class, the octyl is 2-ethylhexyl-.

In one class of this embodiment, $R^1$ is chosen from methyl, ethyl, unbranched or branched propyl, unbranched or branched butyl, unbranched or branched pentyl, unbranched or branched hexyl, unbranched or branched heptyl, unbranched or branched octyl, or unbranched or branched nonyl. In one embodiment, $R^2$ is independently chosen from unbranched or branched butyl, unbranched or branched octyl, or unbranched or branched nonyl.

In one embodiment, $R^2$ is chosen from unbranched or branched propyl, unbranched or branched butyl, unbranched or branched pentyl, unbranched or branched hexyl, unbranched or branched heptyl, or unbranched or branched octyl.

In one embodiment, $R^1$ is chosen from methyl, ethyl, unbranched or branched propyl, unbranched or branched butyl, unbranched or branched pentyl, unbranched or branched hexyl, unbranched or branched heptyl, unbranched or branched octyl, or unbranched or branched nonyl. In one class of this embodiment, $R^1$ is methyl. In one class of this embodiment, $R^1$ is ethyl. In one class of this embodiment, $R^1$ is unbranched or branched propyl. In one class of this embodiment, $R^1$ is unbranched or branched butyl. In one class of this embodiment, $R^1$ is unbranched or branched pentyl. In one class of this embodiment, $R^1$ is unbranched or branched hexyl. In one class of this embodiment, $R^1$ is unbranched or branched heptyl. In one class of this embodiment, $R^1$ is unbranched or branched octyl. In one subclass of this class, octyl is 2-ethylhexyl-. In one class of this embodiment, $R^1$ is unbranched or branched nonyl. In one embodiment, $R^1$ is chosen from unbranched or branched butyl, unbranched or branched octyl or unbranched or branched nonyl.

In one embodiment, $R^1$ is unbranched or branched butyl; and $R^2$ is unbranched or branched octyl. In one class of this embodiment, $R^1$ is n-butyl; and $R^2$ is 2-ethylhexyl.

In one embodiment, n is 1. In one embodiment, n is 2. In one embodiment, n is 3. In one embodiment, each n is 1 or 2.

In one embodiment, the compound of formula I is chosen from

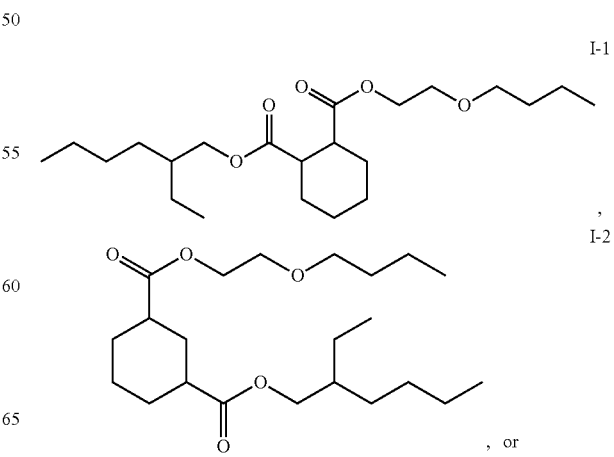

, or

-continued

I-3
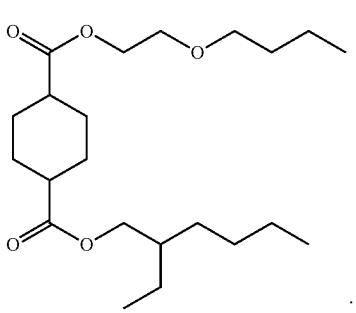

In one class of this embodiment, the compound of formula I is

I-1
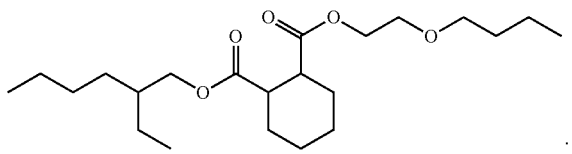

In one class of this embodiment, the compound of formula I is

I-2
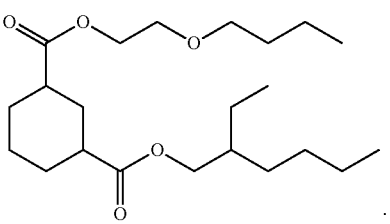

In one class of this embodiment, the compound of formula I is

I-3
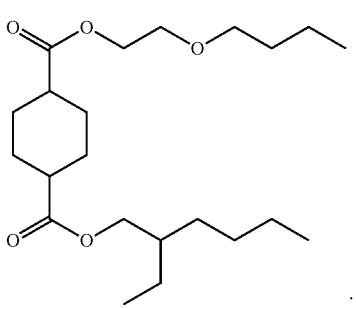

Plasticizer Composition

The present application discloses a plasticizer composition comprising: greater than 40 weight percent ("wt %") of a compound of formula I:

I
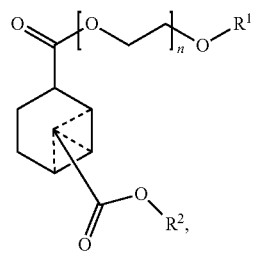

less than 30 wt % of a compound of formula II:

II
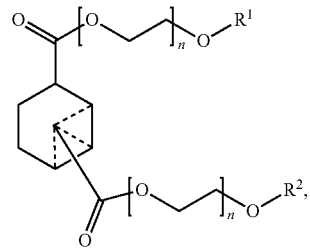

and less than 40 wt % of a compound of formula III:

III
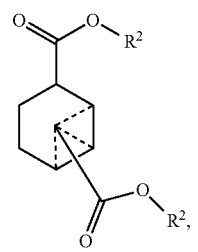

wherein: each $R^1$ is independently unbranched or branched $(C_{1-9})$alkyl; each $R^2$ is independently unbranched or branched $(C_{1-12})$alkyl; and each n is independently 1, 2 or 3, wherein the wt % is determined based on the total weight of the plasticizer composition.

In one embodiment, wherein the compound of formula I is Ia:

Ia
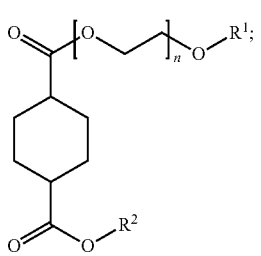

the compound of formula II is IIa:

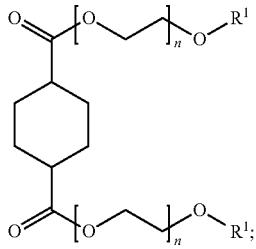

and the compound of formula III is IIIa:

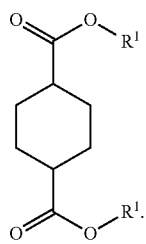

In one class of this embodiment, the compound of formula II is present at less than 25 wt %. In one subclass of this class, the compound of formula III is present at less than 30 wt %.

In one embodiment, wherein the compound of formula I is Ib:

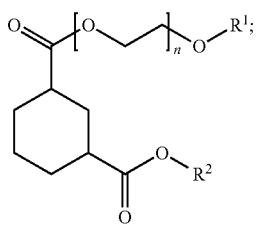

the compound of formula II is IIb:

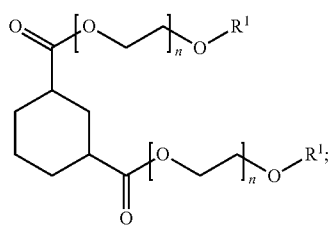

and the compound of formula III is IIIb:

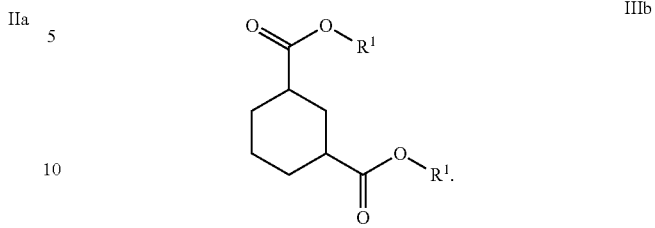

In one class of this embodiment, the compound of formula II is present at less than 25 wt %. In one class of this embodiment, the compound of formula II is present at less than 20 wt %. In one class of this embodiment, the compound of formula II is present at less than 16 wt %.

In one embodiment, the compound of formula I is Ic:

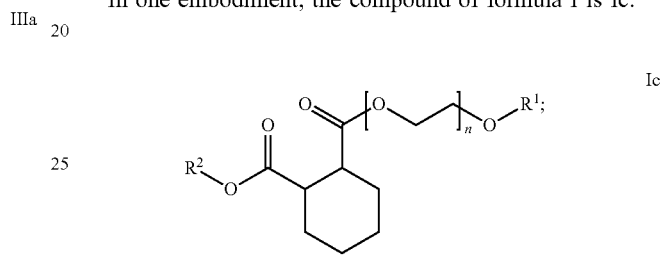

the compound of formula II is IIc:

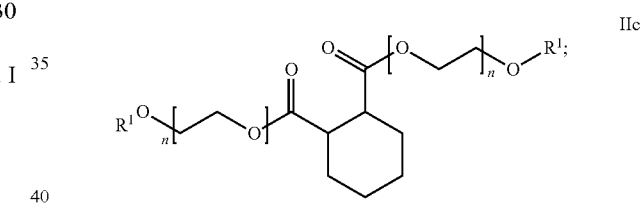

and the compound of formula III is IIIc:

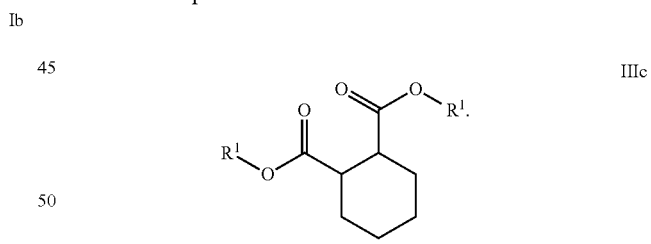

In one class of this embodiment, the compound of formula II is present at less than 25 wt %. In one class of this embodiment, the compound of formula II is present at less than 20 wt %. In one class of this embodiment, the compound of formula II is present at less than 18 wt %.

In one embodiment, each $R^1$ is independently chosen from methyl, ethyl, unbranched or branched propyl, unbranched or branched butyl, unbranched or branched pentyl, unbranched or branched hexyl, unbranched or branched heptyl, unbranched or branched octyl, or unbranched or branched nonyl. In one class of this embodiment, each $R^1$ is independently chosen from unbranched or branched butyl, unbranched or branched octyl or unbranched or branched nonyl. In one class of this embodiment, each $R^1$ is methyl. In one class of this embodiment, each $R^1$ is ethyl. In one class of this embodiment, each $R^1$ is unbranched or branched propyl. In one class of this embodiment, each $R^1$ is unbranched or branched butyl. In one class of this embodiment, each $R^1$ is unbranched or branched pentyl. In one class of this embodiment, each $R^1$ is unbranched or branched hexyl. In one class of this embodiment, each $R^1$ is unbranched or branched heptyl. In one class of this embodiment, each $R^1$ is unbranched or branched octyl. In one subclass of this class, the octyl is 2-ethylhexyl. In one class of this embodiment, each $R^1$ is unbranched or branched nonyl.

In one embodiment, each $R^2$ is independently chosen from unbranched or branched propyl, unbranched or branched butyl, unbranched or branched pentyl, unbranched or branched hexyl, unbranched or branched heptyl, unbranched or branched octyl, unbranched or branched nonyl, unbranched or branched decyl, or unbranched or branched undecanyl, or unbranched or branched dodecanyl. In one class of this embodiment, each $R^2$ is unbranched or branched propyl. In one class of this embodiment, each $R^2$ is unbranched or branched butyl. In one class of this embodiment, each $R^2$ is unbranched or branched pentyl. In one class of this embodiment, each $R^2$ is unbranched or branched hexyl. In one class of this embodiment, each $R^2$ is octyl. In one subclass of this class, the octyl is 2-ethylhexyl. In one class of this embodiment, each $R^2$ is unbranched or branched nonyl. In one class of this embodiment, each $R^2$ is unbranched or branched decyl. In one class of this embodiment, each $R^2$ is unbranched or branched undecanyl. In one class of this embodiment, each $R^2$ is unbranched or branched dodecanyl.

In one class of this embodiment, $R^1$ is chosen from methyl, ethyl, unbranched or branched propyl, unbranched or branched butyl, unbranched or branched pentyl, unbranched or branced hexyl, unbranched or branched heptyl, unbranched or branched octyl, or unbranched or branched nonyl.

In one embodiment, each $R^2$ is independently chosen from unbranched or branched propyl, unbranched or branched butyl, unbranched or branched pentyl, unbranched or branched hexyl, unbranched or branched heptyl, unbranched or branched octyl or unbranched or branched nonyl. In one class of this embodiment, each $R^2$ is independently chosen from unbranched or branched butyl, unbranched or branched octyl, or unbranched or branched nonyl.

In one class of this embodiment, $R^1$ is chosen from methyl, ethyl, unbranched or branched propyl, unbranched or branched butyl, unbranched or branched pentyl, unbranched or branced hexyl, unbranched or branched heptyl, unbranched or branched octyl, or unbranched or branched nonyl.

In one embodiment, $R^1$ is unbranched or branched butyl; and $R^2$ is unbranched or branched octyl. In one class of this embodiment, $R^1$ is n-butyl; and $R^2$ is 2-ethylhexyl.

In one embodiment, each n is 1. In one embodiment, each n is 2. In one embodiment, each n is 3. In one embodiment, each n is 1 or 2.

In one embodiment, the compound of formula II is present at less than 25 wt %. In one class of this embodiment, the compound of formula III is present at less than 30 wt %. In one embodiment, the compound of formula II is present at less than 20 wt %. In one embodiment, the compound of formula II is present at less than 18 wt %. In one embodiment, the compound of formula II is present at less than 16 wt %.

In one embodiment, the compound of formula III is present at less than 30 wt %.

Resin Compositions

The present application discloses a composition comprising: (I) a resin; and (II) a plasticizer composition comprising: greater than 40 weight percent ("wt %") of a compound of formula I:

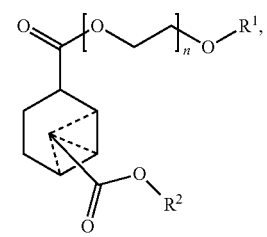

I less than 30 wt % of a compound of formula II

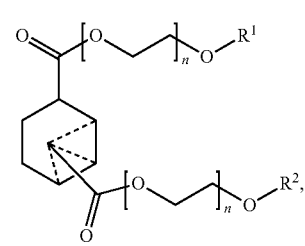

II and less than 40 wt % of a compound of formula III

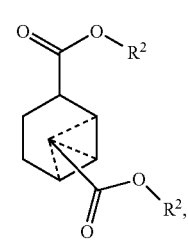

III wherein: each $R^1$ is independently unbranched or branched $(C_{1-9})$alkyl; each $R^2$ is independently unbranched or branched $(C_{1-12})$alkyl; and each n is independently 1, 2 or 3, wherein the wt % is determined based on the total weight of the plasticizer composition.

In one embodiment, $R^2$ is $(C_{3-9})$alkyl.

In one embodiment, the compound of formula I is

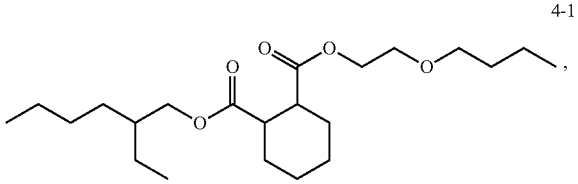 [SMILES: CCCCOCCOC(=O)C1CCCCC1C(=O)OCC(CC)CCCC]

4-1 the compound of formula II is

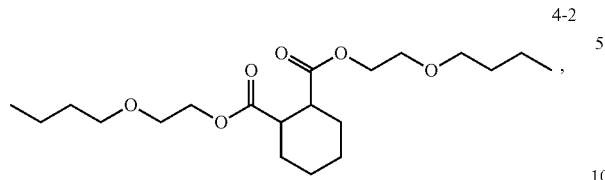
4-2 and the compound of formula III

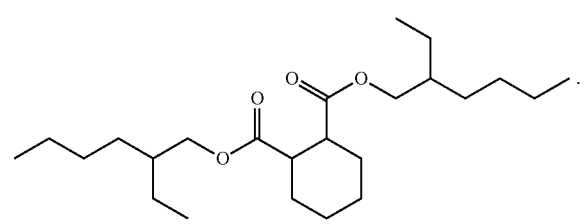
4-3

In one embodiment, the compound of formula I is

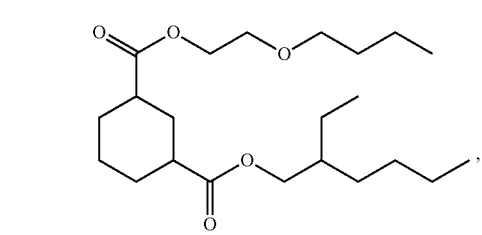
5-1 the compound of formula II is

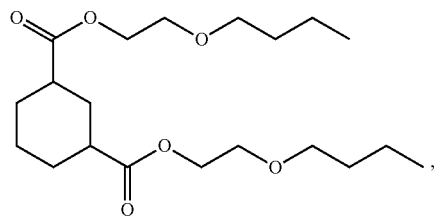
5-2 and the compound of formula III is

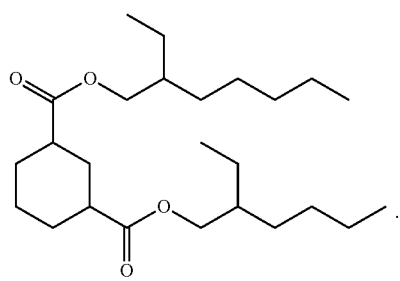
5-3

In one embodiment, the compound of formula I is 6-1 the compound of formula II is 6-2 and the compound of formula III is 6-3

In one embodiment, the composition further comprises other components chosen from a filler, a flame retardant, a stabilizer, a pigment, a processing aid, another plasticizer, or combinations.

In one embodiment, the another plasticizer may comprise phthalates; terephthalates; isophthalates; trimellitates; adipates; cyclohexanedicarboxylates; benzoates; phosphates; diesters of ethylene glycol, propylene glycol, their oligomers, and mixtures thereof; citrates; succinates; alkyl sulfonates; fatty acid esters and epoxidized fatty acid esters; triglycerides and epoxidized triglycerides, optionally substituted; dianhydrohexitol diesters; pentaerythritol-based tet raesters; furan-based esters; other esters; ketals; and/or other polymeric plasticizers. In one embodiment, the another plasticizer may comprise dioctyl terephthalate, diisooctyl phthalate, di-2-ethylhexyl phthalate, di-2-ethylhexyl terephthalate, tri-2-ethylhexyl trimellitate, di-2-propylheptyl phthalate, diisononyl phthalate, diisodecyl phthalate, diisoundecyl phthalate, di-butyl terephthalate, dipentyl terephthalate, ditridecyl phthalate, trioctyl trimellitate, triisononyl trimellitate, 2,2,4-trimethyl-1,3-pentanediol diisobutyrate, isononyl benzoate, isodecyl benzoate, diisononyl 1,2-cyclohexanedicarboxylate, dioctyl adipate, di-2-ethylhexyl adipate, triethylene glycol di-2-ethylhexanoate, diethylene glyco dibenzoate, dipropylene glycol dibenzoate, and/or dibenzoates produced from mixtures of diethylene glycol and dipropylene glycol. In one aspect, the second plasticizer comprises dioctyl terephthalate, di-2-ethylhexyl terephthalate, dioctyl adipate, di-2-ethylhexyl adipate, and/or triethylene glycol di-2-ethylhexanoate. In one embodiment, the additional plasticizers may comprise, di-2-ethylhexyl terephthalate, diisononyl phthalate, di-butyl terephthalate, and/or diisononyl 1,2-cyclohexanedicarboxylate.

EXAMPLES

Abbreviations

Avg is average; Comp is composition; cP is centipoise; ° C. is degree(s) Celsius; ° F. is degree(s) Fahrenheit; DOTP is bis(2-ethylhexyl) terephthalate; EB is 2-butoxyethan-1-ol; 2EH is 2-ethylhexan-1-ol; Ex is example(s); g is gram(s); GC is gas chromatography; h or hr is hour(s); L is liter; min is minute(s); mL or ml is milliliter; mm is millimeter(s); mol is mole(s); Nm is newton meter; phr is parts per hundred parts polymer; psig is pounds per square inch; Pz is plasticizer; rpm is revolutions per minute; PVC is polyvinyl chloride; rt is room temperature; tR is retention time; s or sec is second(s); Temp is temperature; wt % is weight percent;

Compound B can be synthesized from reacting a mixture of alcohols with either an ester or acid A. Alternatively, Compound B can be synthesized from a sequential esterification process. The reaction can be a direct esterification reaction of the diacid or by an ester exchange reaction. Compound C can be obtained by the selective hydrogenation of the aromatic ring of compound C by use of a catalyst. Alternatively, the compound A can be hydrogenated before the esterification.

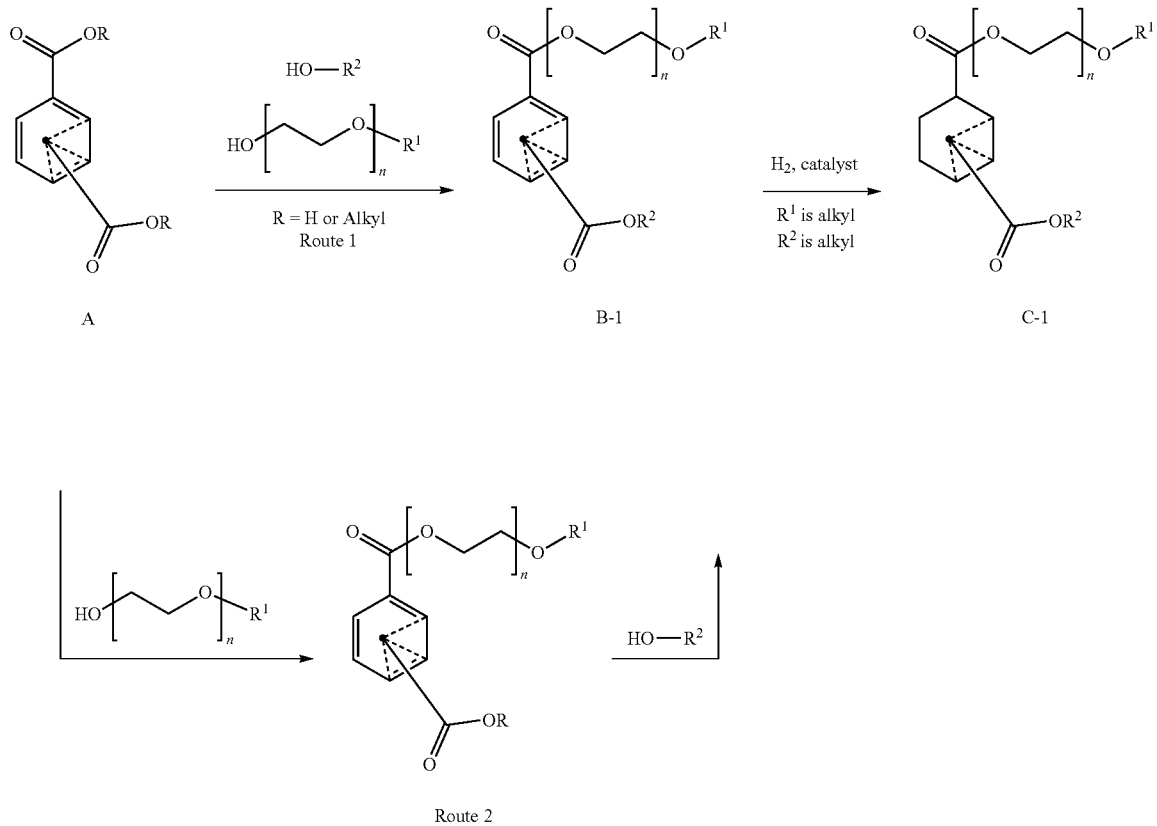

Scheme 1. Synthetic scheme for preparing the mixed ester plasticizers.

When carrying out the esterification of compound A using a one-pot step, a mixture of products is expected based on the ratio of the alcohols. The expected products for the esterification are provided below in scheme 2.

Scheme 2. Synthetic scheme for hydrogenation of the mixed ester plasticizer.

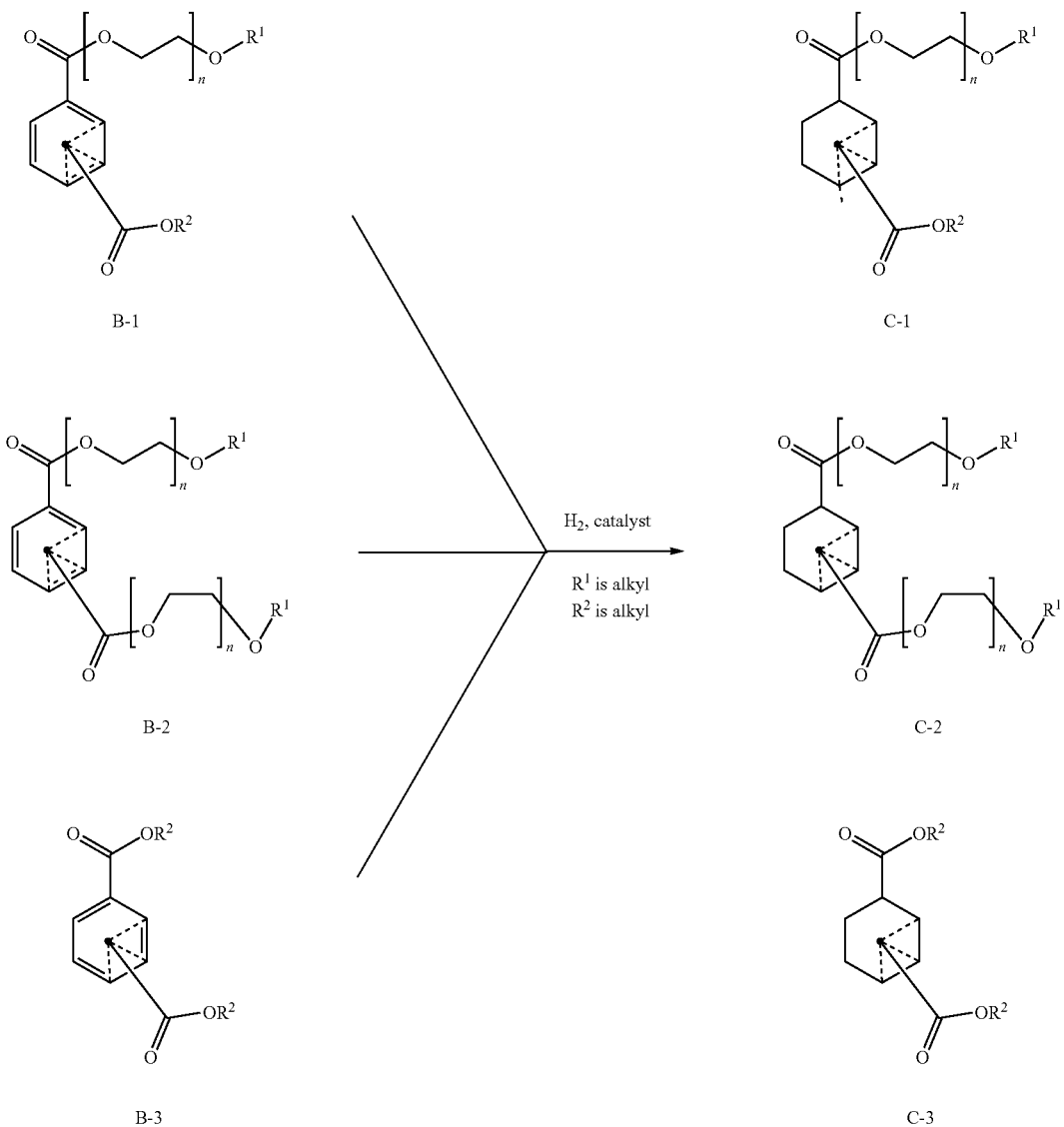

Synthesis of Composition 3

2-butoxyethan-1-ol (295.5 g, 2.5 mol), 2-ethylhexan-1-ol (325.6 g, 2.5 mol), dimethyl terephthalate (388.4 g, 2 mole), and tetraisopropyl titanate (0.505g, 500 ppm) were combined in a round bottom flask equipped with a Dean-Stark apparatus. The reaction mixture was heated to reflux to remove the generated methanol (-166 mL). The reaction mixture was concentrated in vacuo (150° C., <5 mmHg). The resulting crude product was treated with 2.5% aq. NaOH, and the mixture was heated at 90° C. (30 min). The aqueous layer was separated, and the organic layer was treated with water (300 g) and the mixture was heated at 90° C. (30 min). The organic layer was separated, and the organic was filtered through diatomaceous earth. The organic layer was then concentrated in vacuo (~3 mmHg) for 20 minutes. Then the material was treated with activated carbon (0.5 g) and stirred at 90° C. (30 min), and the mixture was filtered through diatomaceous earth to provide Composition 3. In a similar, dimethyl terephthalate was substituted with phthalic anhydride to prepare Composition 1, and the isophthalic acid to prepare Composition 2 (Table 1).

General Hydrogenation Step

The resulting ester compositions were hydrogenated in a 2 L 316 SS autoclave. Ten grams of a Pd-Ni/Al2O3 catalyst was loaded into a SS mesh basket and attached to the thermowell within the reactor. Then approximately 1 kg of the feed ester described in Table 1 was added to the reactor body and the head installed. The head space was vented with $N_2$, pressurized to 200 psig H2, then heated to reaction temperature of 210° C. while stirring at 200 rpm. Once at the temperature set point additional $H_2$ was added to a pressure of 1500 psig and the stir speed increased to 1200 rpm to start the reaction. The reaction progress could be tracked by either GC analysis of the product collected through a dip tube or by watching the $H_2$ consumption. Ring saturation conversion >98% took approximately 4 hours at these conditions for the synthetic targets. Table 2 provides the compositions synthesized.

The samples were converted to the trimethylsilyl derivatives, and the derivatives were subjected to gas chromatography for separation. The mass of the samples was determined by mass spectrometry.

The GCMS used for this work included a Thermo DSQII XL single quad mass spectrometer to collect mass spectral data in EI (electron ionization) mode. In addition, molecular weights were confirmed by ammonia chemical ionization.

The gas chromatograph used with the mass spectrometer was a Thermo Trace Ultra GC with Tri Plus XL autosampler. The GC Column was a 30 m DB-1701 with 0.25 mm inner diameter and 0.25 micron film thickness. The GC oven was programmed from 100° C-280° C. at 6° C./min and held for 5 min at 280° C. The GC injection port was held at 280° C. with a split flow of 150 mL min helium. The column flow rate was set to 1.5 mL/min helium in constant flow mode, with vacuum compensation from the mass spec. Samples were prepared by placing three drops of sample in 1.5 mL acetone. After sample preparation, 0.3 microliters were injected directly on the GCMS instrument using the autosampler.

Integration was performed to calculate approximate area percent values assuming equal detector response among all analytes and that all sample components elute from the chromatographic column.

Samples were analyzed in both electron ionization (EI) and chemical ionization (CI) modes. In EI mode, the instrument scanned from 18-550 amu at 250° C. In CI mode, ammonia was used as a reagent gas to confirm molecular weights and the instrument scanned from 80-600 amu at 250° C. with an ammonia flow rate of approximately 1.2 mL/min.

TABLE 1

Synthesis of Comp 1, 2, and 3.

| Comp # | Starting Materials | GC Determined Composition | | |
|---|---|---|---|---|
| | | Mixed Ester (wt %, tR) | EB Ester (wt %, tR) | 2EH ester (wt %, tR) |
| 1 | 2-butoxyethan-1-ol, 2-ethylhexan-1-ol, Phthalic Anhydride | Ex 1-1 (44.77, 28.41) | Ex 1-2 (16.9, 28.27) | Ex 1-3 (37.61, 28.5) |
| 2 | 2-butoxyethan-1-ol, 2-ethylhexan-1-ol, Isophthalic Acid | Ex 2-1 (44.24, 29.53) | Ex 2-2 (15.34, 29.15) | Ex 2-3 (40.43, 29.90) |
| 3 | 2-butoxyethan-1-ol, 2-ethylhexan-1-ol, Dimethyl terephthalate | Ex 3-1 (48.0, 30.16) | Ex 3-2 (15.6, 29.64) | Ex 3-3 (35.7, 30.68) |

Table 2 provides the compositions after subjecting the unsaturated intermediates to hydrogenation. Two retention times were observed for each due to cis/trans isomers.

TABLE 2

| Comp | Starting Comp # | GC Determined Composition | | |
|---|---|---|---|---|
| | | Mixed Ester (wt %, tR) M+ | EB Ester (wt %, tR) M+ | 2EH ester (wt %, tR) M+ |
| 4 | 1 | Ex 4-1 (42.78, 26.97/27.061) 384 | Ex 4-2 (17.71, 26.77/26.83) 372 | Ex 4-3 (39.52, 27.13/27.22) 396 |
| 5 | 2 | Ex 5-1 (43.87, 27.89/28.64) 384 | Ex 5-2 (15.04, 27.54/28.26) 372 | Ex 5-3 (39.66, 28.99/29.88) 396 |
| 6 | 3 | Ex 6-1 (46.86, 28.38/29.23) 384 | Ex 6-2 (24.75, 27.98/28.76) 372 | Ex 6-3 (28.38, 28.76/29.68) 396 |

TABLE 3

Table 3 provides the structures for the compounds synthesized.

| Unsaturated Ester | Saturated Ester |
|---|---|

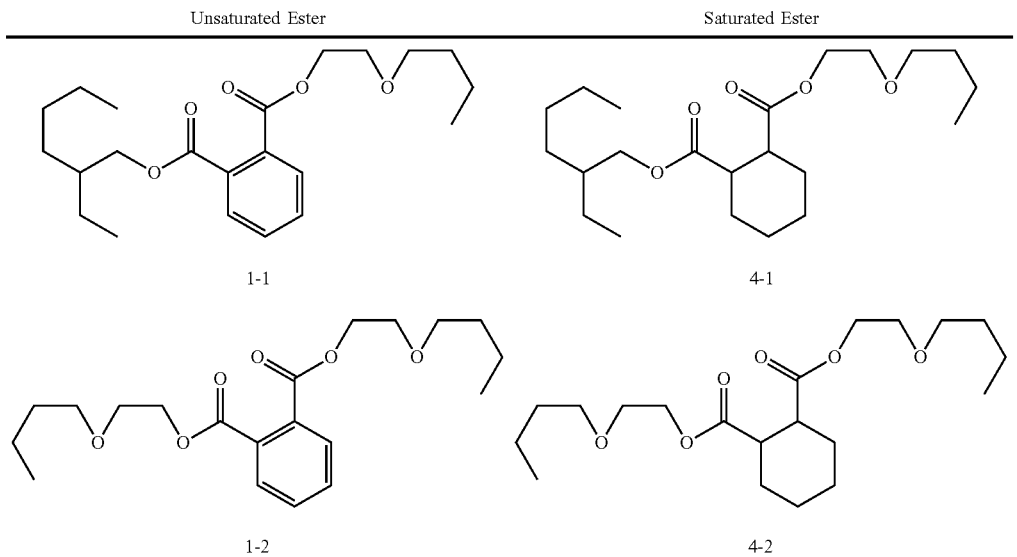

1-1  4-1

1-2  4-2

TABLE 3-continued

Table 3 provides the structures for the compounds synthesized.

| Unsaturated Ester | Saturated Ester |
|---|---|
| 1-3 | 4-3 |
| 2-1 | 5-1 |
| 2-2 | 5-2 |
| 2-3 | 5-3 |
| 3-1 | 6-1 |

TABLE 3-continued

Table 3 provides the structures for the compounds synthesized.

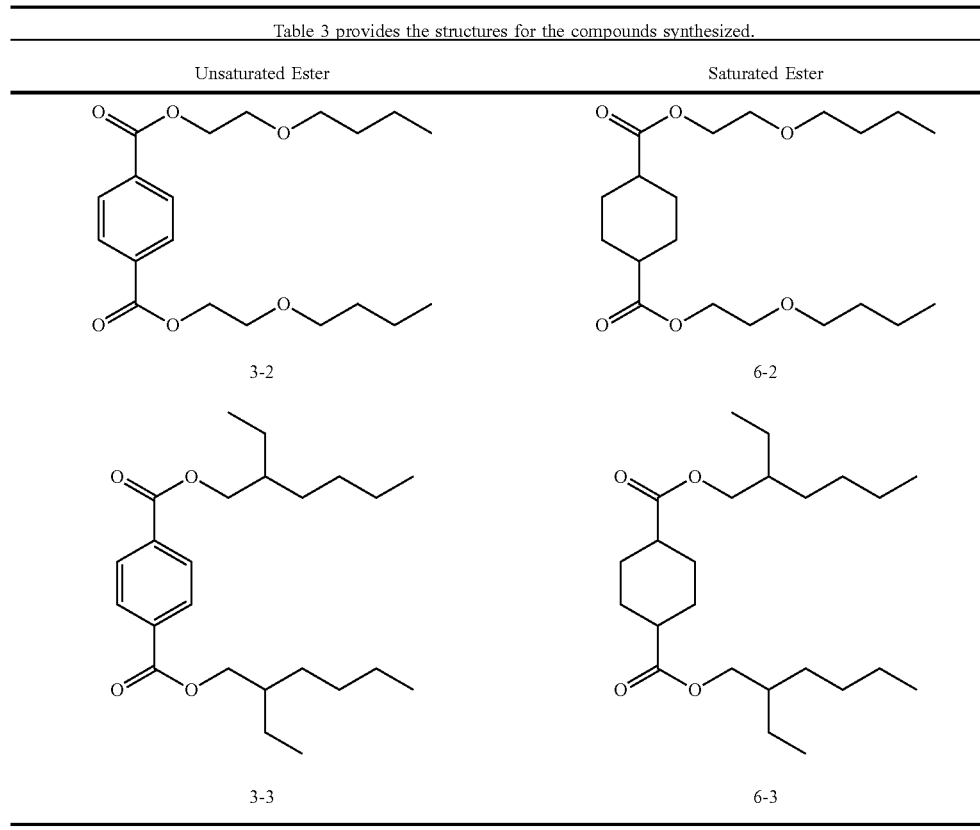

Plastisol Formulation

The standard formulation, shown in Table 4, was used for the plastisol evaluation. The plastisols were prepared by combining the components of the formulation, shown in Table 4, into an appropriate Flack Tek mixing container. Each sample was agitated using a Flack Tek DAC 600.2 VAC Speed MixerTM operated at 1600 rpm for 40 sec intervals. Temperature was monitored between mixing intervals to ensure the temperature did not rise above 95° F. Once samples were thoroughly mixed to a smooth consistency, they were then deaerated for 5 minutes under vacuum (~75 Torr) at 1000 rpm.

TABLE 4

Standard Plastisol Formulation Used for Studies.

| Component | Phr |
| --- | --- |
| Plasticizer | 60 |
| Geon 121A (PVC Homopolymer Dispersion Resin) | 100 |
| Drapex 6.8 (ESO) | 3 |
| Akrostab Stabilizers LT-4798 | 3 |

Viscosity

The Brookfield Viscosity was determined according to ASTM D1824. After preparing the plastisols, the plastisols were transferred to a separate container to measure viscosity. The appropriate spindles were used to measure viscosities at 2 rpm and 20 rpm. Measurements were taken at time=24 and 192 h at rt.

Table 5 shows the Brookfield viscosity results at 2 rpm and at 20 rpm. The Brookfield viscosity results for DOTP is provided for comparison.

At 2 rpm, the plastisols prepared from Comp 4 and 5 show significant viscosity gains, whereas the plastisol prepared from Comp 6 showed minimal change. Similar trends were observed in the 20 rpm viscosity data.

TABLE 5

| | Brookfield Viscosity | | | |
| --- | --- | --- | --- | --- |
| Comp | 1 day, 2 rpm Viscosity (cP) | 8 days, 2 rpm Viscosity (cP) | 1 day, 20 rpm Viscosity (cP) | 8 days, 20 rpm Viscosity (cP) |
| 4 | 3460 | 5180 | 2240 | 3000 |
| 5 | 5140 | 6480 | 2605 | 3330 |
| 6 | 2040 | 1644 | 2540 | 1910 |
| DOTP | 3540 | 4400 | 2820 | 3190 |

Efficiency

The shore A hardness was determined according to ASTM D2240. Fused parts were prepared using 25 g of plastisol in a circular button mold. The parts are fused at 375° F. for 30 min, removed from the mold, and allowed to equilibrate at rt for 24 h. Hardness was measured on a Rex Durometer. The instrument was calibrated for the expected range of hardness using the appropriate calibration standard.

Table 6 shows the hardness results for the various plasticizer samples. Hardness is a measure of the efficiency of the plasticizer, which is the plasticizer's ability to soften the flexible PVC, with lower hardness value equating to higher efficiency. According to ASTM D2240, a difference of 2 units represents a statistically significant difference. The data indicates that the iso and para isomers are more efficient than the DOTP control.

TABLE 6

Shore A hardness data.

| Comp | Shore A Hardness |
|---|---|
| 4 | 70.1 |
| 5 | 67.5 |
| 6 | 68.1 |
| DOTP | 73.1 |

Gel Point

Fusion results were determined using DHR-1 Parallel Plate Rheometer and adapting ASTM D2538. Samples were analyzed on a TA Instruments DHR-1 parallel plate rheometer, fitted with an Environmental Test Chamber, 25 mm parallel plate geometry, set to a 1000-micron gap. A temperature sweep from 104-302° F. is run in oscillation mode with a heating rate of 41° F./min. On the resulting plots, the temperature where the G'/G" curves cross is taken as an indication of the "gel" point.

Table 7 shows the gel point results for the plasticizers tested. Typically, higher compatibility plasticizers yield lower gel points. In this data set the plasticizers for this study all perform better than the DOTP control.

TABLE 7

Fusion Characteristics

| Comp | Gel point (° C.) |
|---|---|
| 4 | 68 |
| 5 | 66 |
| 6 | 67 |
| DOTP | 83 |

Loop Spew

The loop spew data was determined according to ASTM D3291. Approximately 110 g of sample is poured into a twin film dagger mold. A thermocouple is inserted into the plastisol to monitor internal temperature. The mold is then placed in a heating block set to 375° F. Once the plastisol reaches target temperature (338° F.) the mold is removed from the heating block and set aside to cool. Vinyl strips approximately 70 mils thick are cut from the sheets. Strip samples are allowed to equilibrate for 24 h at room temperature before loop spew exudation testing. Twelve strips each are cut into 1.5-inch X 0.5-inch sections and placed into loop spew testing jig. Four samples are removed from the jig at specified intervals, 4 h, 1 day, and 7 days, and tested. Exudation is rated on a scale of 0-3 with higher value indicating greater exudation.

An important performance attribute of any plasticizer is its ability to stay in the PVC matrix. Incompatibility with any of the components of a formulation can cause the plasticizer to migrate to the surface of the PVC part, also known as exudation. The formulation tested here has a minimal number of components, so the exudation results are highly indicative of the plasticizers compatibility with the resin itself. Table 8 provides the loop spew results for the plasticizers tested. It is not uncommon for a PVC part to "settle in," where it may show exudation at the four-hour mark but exhibit no such tendencies at longer time intervals. In this particular case, the molecules tested all exhibit better exudation performance than the standard general-purpose plasticizer, DOTP.

TABLE 8

Loop Spew Results

| Comp | 4 hr Avg | 24 hr | 7 days |
|---|---|---|---|
| 4 | 1 | 1 | 0 |
| 5 | 1 | 0 | 0 |
| 6 | 1 | 0 | 0 |
| DOTP | 0.5 | 1.5 | 2.25 |

Neat Plasticizer Volatility

The neat plasticizer volatility was determined according to EPA method 24 using 110° C./60min parameters.

Table 9 provides the volatility of the plasticizers.

TABLE 9

| Comp | VOC g (std dev) |
|---|---|
| 4 | 2.4 (0.2) |
| 5 | 2.0 (0.2) |
| 6 | 2.2 (0.3) |
| DOTP | 0.4 (0.1) |

Dry Blend Preparation and Testing

The disclosed plasticizers were also formulated into dry blends using the standard formulation provided in Table 10.

The components are weighed into the appropriate mixing cup and agitated using a Flack Tek DAC 600.2 VAC Speed Mixer ™ operated at 1200 rpm for 60 sec. The samples were mixed for four cycles to ensure homogeneity of the dry blend.

TABLE 10

Dry Blend Formulation Used for Studies.

| Component | phr |
|---|---|
| Plasticizer | 50 |
| OxyVinyls Oxy 240F suspension resin | 100 |
| Burgess Clay | 17 |

The fusion test using a Brabender Torque Rheometer is adapted from ASTM D2538-02 "Standard Practice for Fusion of Poly(Vinyl Chloride) (PVC) Compounds Using a Torque Rheometer." The torque rheometer is fitted with a 60 mL bowl and roller mixing blades. The rheometer is programmed to run a temperature ramp from 40° C. to 150° C. over 22 min.

The plasticizers in this project were evaluated using the above method and the results are tabulated in Table 11.

TABLE 11

Brabender Fusion Data For Dry Blend

| Comp | Fusion Time (min) | Torque (Nm) | Fusion Temp (° C.) |
|---|---|---|---|
| 4 | 15.5 | 23.2 | 112.8 |
| 5 | 17.3 | 27.1 | 113.5 |
| 6 | 16.1 | 23.8 | 115.3 |
| DOTP | 16.9 | 24.1 | 117.6 |

Other embodiments will be apparent to those skilled in the art from consideration of the specification and practice of the embodiments disclosed herein. It will be understood that variations and modifications can be effected within the spirit and scope of the disclosed embodiments. It is further

What is claimed is:

1. A plasticizer composition comprising:
    greater than 40 weight percent (wt %) of a compound of formula I:

[Structure I]

20-30 wt % of a compound of formula II:

[Structure II]

and
    20-40 wt % of a compound of formula III:

[Structure III]

wherein:
        each $R^1$ is independently an unbranched or branched $(C_{1-9})$alkyl;
        each $R^2$ is independently an unbranched or branched $(C_{1-12})$alkyl; and
        each n is independently 1, 2 or 3,
    wherein the wt % is determined based on the total weight of the plasticizer composition.

2. The plasticizer composition of claim 1, wherein: each $R^2$ is independently chosen from unbranched or branched propyl, unbranched or branched butyl, unbranched or branched pentyl, unbranched or branched hexyl, unbranched or branched heptyl, unbranched or branched octyl, unbranched or branched nonyl, unbranched or branched decyl, unbranched or branched undecanyl, or unbranched or branched dodecanyl.

3. The plasticizer composition of claim 1, wherein: the compound of formula I is

[Structure 4-1]

the compound of formula II is

[Structure 4-2]

and
    the compound of formula III is

[Structure 4-3]

4. The plasticizer composition of claim 1, wherein: the compound of formula I is

[Structure 5-1]

the compound of formula II is

[Structure 5-2]

and
the compound of formula III is

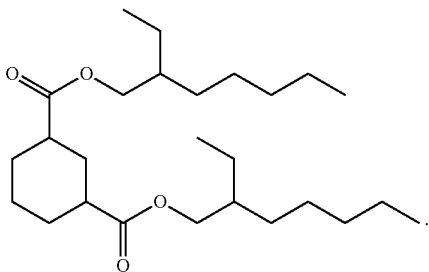

5. The plasticizer composition of claim 1, wherein:
the compound of formula I is

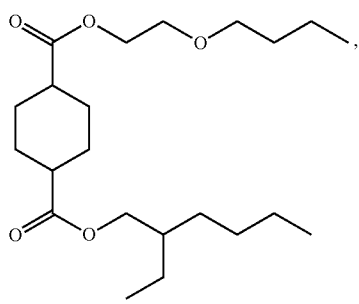

the compound of formula II is

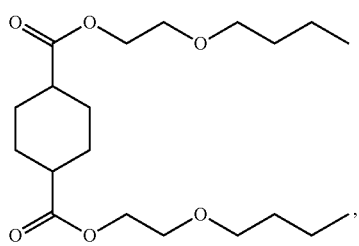

and
the compound of formula III is

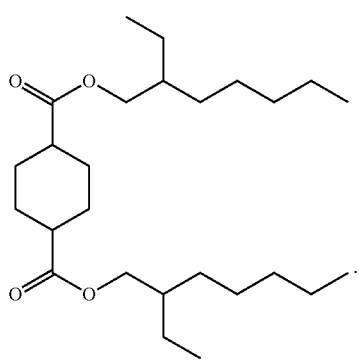

6. A resin composition comprising:
(I) a resin; and
(II) a plasticizer composition comprising:
greater than 40 weight percent ("wt %") of a compound of formula I:

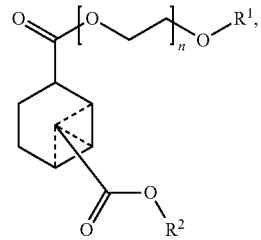

20-30 wt % of a compound of formula II

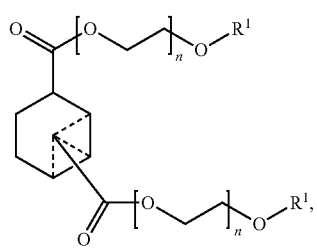

and
20-40 wt % of a compound of formula III

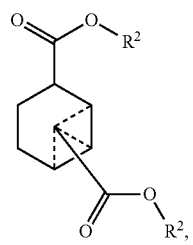

wherein:
each $R^1$ is independently unbranched or branched $(C_{1-9})$alkyl;
each $R^2$ is independently unbranched or branched $(C_{1-12})$alkyl; and
each n is independently 1, 2 or 3,
wherein the wt % is determined based on the total weight of the plasticizer composition.

7. The resin composition of claim 6, wherein: each $R^2$ is independently chosen from unbranched or branched propyl, unbranched or branched butyl, unbranched or branched pentyl, unbranched or branched hexyl, unbranched or branched heptyl, unbranched or branched octyl, unbranched or branched nonyl, unbranched or branched decyl, unbranched or branched undecanyl, or unbranched or branched dodecanyl.

8. The resin composition of claim 6, wherein:
the compound of formula I is

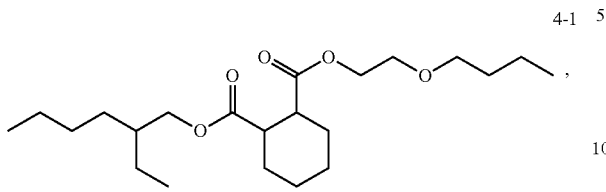
4-1 the compound of formula II is

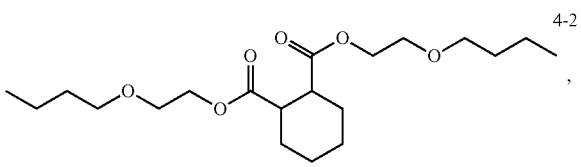 [SMILES: CCCCOCCOC(=O)C1CCCCC1C(=O)OCCOCCCC]
4-2 and
the compound of formula III is

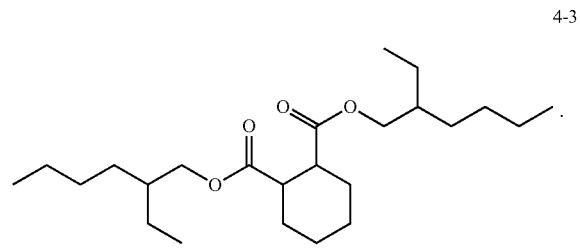 [SMILES: CCCCC(CC)COC(=O)C1CCCCC1C(=O)OCC(CC)CCCC]
4-3

9. The resin composition of claim 6, wherein:
the compound of formula I is

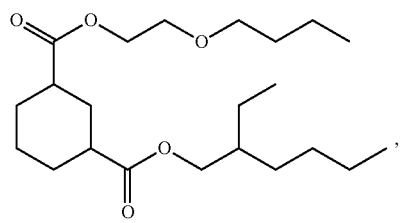
5-1 the compound of formula II is

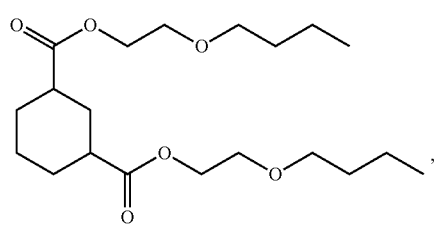
5-2 and
the compound of formula III is

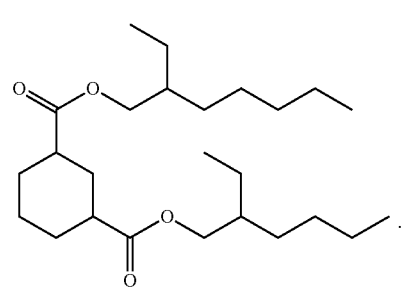
5-3

10. The resin composition of claim 6, wherein:
the compound of formula I is

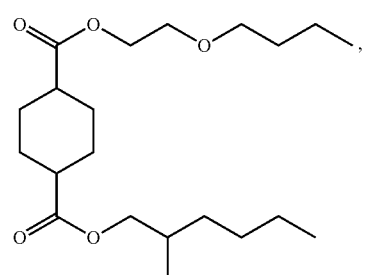
6-1 the compound of formula II is

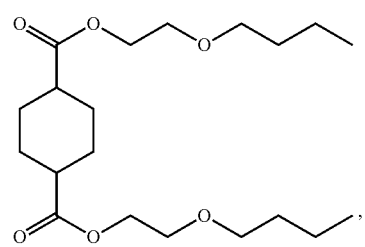
6-2 and
the compound of formula III is

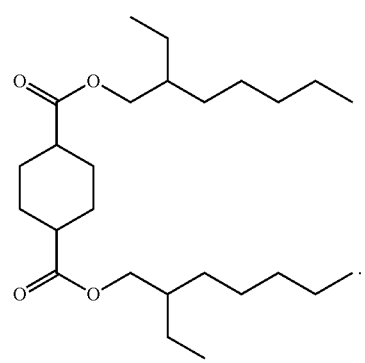
6-3

11. The resin composition of any one of claims 8-10, wherein the resin comprises a polyvinyl chloride, a polyvinyl acetate, an acrylic polymer, vinyl chloride-containing copolymers, or combinations thereof.

12. The resin composition of any one of claims 8-10, the composition further comprises other components chosen from a filler, a flame retardant, a stabilizer, a pigment, a processing aid, another plasticizer, or combinations thereof.

13. The resin composition of claim 12, wherein the filler comprises calcium carbonate and/or fly ash, and wherein the stabilizer comprise metal soaps, epoxidized oils, epoxidized fatty acid esters, and/or organotin compounds.

* * * * *